United States Patent
Refsnæs et al.

(10) Patent No.: US 11,554,061 B2
(45) Date of Patent: *Jan. 17, 2023

(54) BED, HOSPITAL BED AND RESILIENT SUPPORT STRUCTURE FOR BED

(71) Applicant: ABLY MEDICAL AS, Ålesund (NO)

(72) Inventors: Jørn Refsnæs, Ålesund (NO); Arve Voldsund, Leinøy (NO); Cato Alexander Bjørkli, Hvalstad (NO); Leila Yousif Circhirillo, Oslo (NO); Kjell Are Furnes, Nesoddtangen (NO)

(73) Assignee: Ably Medical AS, Ålesund (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/347,275

(22) PCT Filed: Oct. 24, 2017

(86) PCT No.: PCT/IB2017/056594
§ 371 (c)(1),
(2) Date: May 3, 2019

(87) PCT Pub. No.: WO2018/083566
PCT Pub. Date: May 11, 2018

(65) Prior Publication Data
US 2019/0274906 A1   Sep. 12, 2019

(30) Foreign Application Priority Data

Nov. 4, 2016 (GB) .................................. 1618658
Apr. 4, 2017 (GB) .................................. 1705426

(51) Int. Cl.
*A61G 7/015*   (2006.01)
*G16H 50/30*   (2018.01)
(Continued)

(52) U.S. Cl.
CPC ............ *A61G 7/015* (2013.01); *A61B 5/1036* (2013.01); *A61B 5/11* (2013.01); *A61B 5/1113* (2013.01);
(Continued)

(58) Field of Classification Search
CPC ...... A61G 7/015; A61G 7/0524; A61G 7/018; A61G 7/057; A61G 2203/30;
(Continued)

(56) References Cited

U.S. PATENT DOCUMENTS 57,560 A * 8/1866 Patton .................... A47C 23/28
                                                      5/211
86,120 A * 1/1869 Almond ............... A47C 23/064
                                                      5/191
(Continued)

FOREIGN PATENT DOCUMENTS

CN   101252906 A   8/2008
CN   201436920 U   4/2010
(Continued)

OTHER PUBLICATIONS

Communication dated Jul. 27, 2020 in connection with European patent application No. 17794427.9, 5 pages.
(Continued)

*Primary Examiner* — Myles A Throop
(74) *Attorney, Agent, or Firm* — Dorsey & Whitney LLP

(57) ABSTRACT

There is described support structures for a bed, and various embodiments of a bed for use in a hospital. In an example, a support structure comprises a plurality of sections, each configured to support a respective part of a body, and a plurality of resilient members that extend in a longitudinal direction from an upper end of the support structure to a lower end of the support structure, wherein a shape and/or
(Continued)

profile of the support structure is determined by a shape and/or profile of the resilient members.

14 Claims, 6 Drawing Sheets

(51) Int. Cl.
    *A61B 5/11*     (2006.01)
    *A61B 5/00*     (2006.01)
    *G16H 20/30*     (2018.01)
    *A61B 5/103*     (2006.01)
    *A61G 7/05*     (2006.01)
    *A61G 7/018*     (2006.01)
    *A61G 7/057*     (2006.01)

(52) U.S. Cl.
    CPC ........... *A61B 5/6891* (2013.01); *G16H 20/30* (2018.01); *G16H 50/30* (2018.01); *A61G 7/018* (2013.01); *A61G 7/057* (2013.01); *A61G 7/0524* (2016.11); *A61G 2203/30* (2013.01); *A61G 2203/34* (2013.01); *A61G 2203/36* (2013.01); *A61G 2203/44* (2013.01); *A61G 2203/46* (2013.01)

(58) Field of Classification Search
    CPC ............ A61G 2203/34; A61G 2203/36; A61G 2203/44; A61G 2203/46; G16H 20/30; G16H 50/30; A47C 23/06–068; A47C 23/22; A47C 23/24; A47C 23/32; A47C 27/16; A47C 23/28; A61B 5/1036; A61B 5/1113; A61B 5/6891; A61B 5/11
    See application file for complete search history.

(56) References Cited

U.S. PATENT DOCUMENTS

| | | | | | |
|---|---|---|---|---|---|
| 643,208 | A * | 2/1900 | Schmidt | ................. | A47C 23/28 5/220 |
| 3,380,088 | A * | 4/1968 | Adesky | ................. | A47C 27/16 5/420 |
| 3,716,875 | A * | 2/1973 | Fehr | ................. | A47C 27/16 297/452.53 |
| 3,877,750 | A * | 4/1975 | Scholpp | ................. | A47C 1/143 297/284.3 |
| 4,164,356 | A * | 8/1979 | Knight | ................. | A47C 1/028 297/1 |
| 5,448,789 | A * | 9/1995 | Shirai | ................. | A47C 20/04 5/613 |
| 5,926,877 | A * | 7/1999 | Lin | ................. | A47C 20/041 5/618 |
| 6,877,816 | B1 * | 4/2005 | Farmont | ................. | A47C 31/126 297/380 |
| 7,823,232 | B2 * | 11/2010 | Tinke | ................. | A61G 7/0573 267/89 |
| 9,173,492 | B1 * | 11/2015 | Fortin | ................. | A47C 1/03261 |
| 9,788,800 | B2 * | 10/2017 | Mayoras, Jr. | ........ | A61B 5/6892 |
| 10,675,755 | B2 * | 6/2020 | Sinibaldi | .............. | A61B 1/0016 |
| 11,197,793 | B2 * | 12/2021 | Refsnæs | .............. | A61B 5/6891 |
| 2005/0172405 | A1 * | 8/2005 | Menkedick | ............ | A61G 7/005 5/618 |
| 2008/0147442 | A1 | 6/2008 | Warner et al. | | |
| 2010/0080431 | A1 | 4/2010 | Datema et al. | | |
| 2010/0094139 | A1 | 4/2010 | Brauers et al. | | |
| 2011/0295065 | A1 * | 12/2011 | Gurusamy | ........... | A61B 1/0057 600/141 |
| 2012/0259248 | A1 | 10/2012 | Receveur | | |
| 2013/0090763 | A1 * | 4/2013 | Simaan | ................. | A61B 34/30 700/258 |
| 2013/0205501 | A1 | 8/2013 | Robertson et al. | | |
| 2014/0020182 | A1 * | 1/2014 | Clenet | .................... | A61G 7/018 5/618 |
| 2014/0289962 | A1 * | 10/2014 | Watkins | .................... | A45F 3/24 5/120 |
| 2017/0252260 | A1 * | 9/2017 | Gummin | ................ | A61H 7/001 |
| 2019/0274905 | A1 | 9/2019 | Refsnæs et al. | | |

FOREIGN PATENT DOCUMENTS

| | | |
|---|---|---|
| CN | 102697615 A | 10/2012 |
| CN | 203954044 U | 11/2014 |
| DE | 202015103036 U1 | 10/2016 |
| EP | 0608635 A1 | 8/1994 |
| EP | 2392304 A1 | 12/2011 |
| GB | 2313540 A | 12/1997 |
| GB | 2319851 A | 6/1998 |
| JP | S57-085280 U | 5/1982 |
| JP | H0650630 U | 7/1994 |
| JP | H1043008 A | 2/1998 |
| JP | 2001293037 A | 10/2001 |
| JP | 2010519948 A | 6/2010 |
| JP | 2010511149 A | 4/2011 |
| JP | 2015522379 A | 8/2015 |
| TW | 333044 U | 6/1998 |
| WO | 2008055173 A2 | 5/2008 |
| WO | 2009135081 A2 | 11/2009 |
| WO | 2014015320 A1 | 1/2014 |
| WO | 2015087204 A1 | 6/2015 |

OTHER PUBLICATIONS

International Search Report and Written Opinion dated Jan. 18, 2018 in connection with PCT/IB2017/056594, 9 pages.

International Search Report and Written Opinion dated Jan. 18, 2018 in connection with PCT/IB2017/056595, 12 pages.

First Office Action dated Oct. 27, 2020 in connection with Chinese patent application No. 201780067314.5, 20 pages including English translation.

Office Action dated Sep. 21, 2021 in connection with Japanese patent application No. 2018-546112, 11 pages including English translation.

* cited by examiner

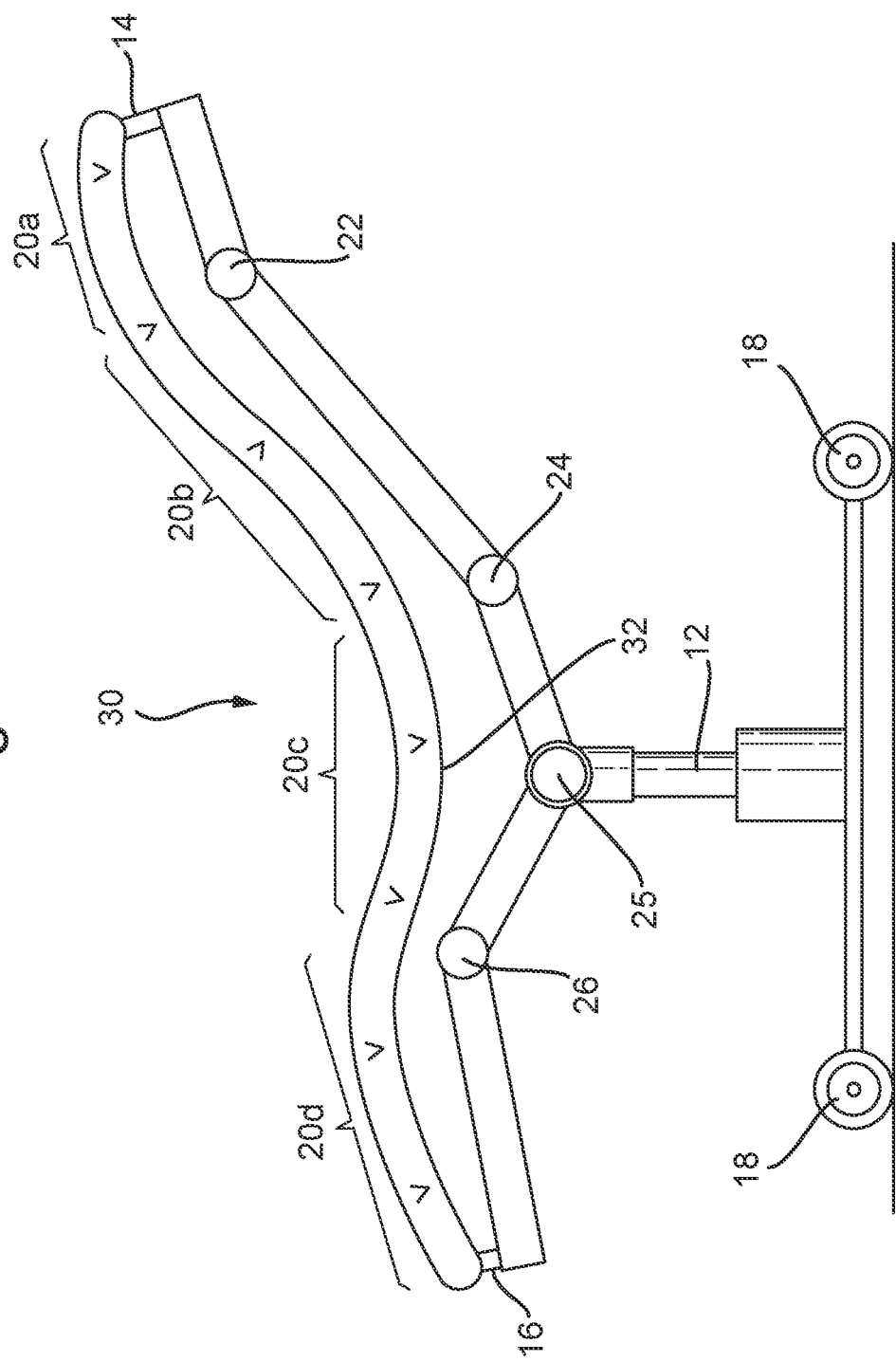

BED, HOSPITAL BED AND RESILIENT SUPPORT STRUCTURE FOR BED

FIELD OF THE INVENTION

The present invention relates generally to technologies, methods and apparatus for and associated with beds for use in a medical or therapeutic environment such as a hospital. In various aspects and embodiments the invention relates to medical, e.g., hospital beds and, more specifically, methods associated with the comfort and movement of patients resting on such beds.

BACKGROUND

The types of beds used in hospitals varies widely and can range from a simple structure comprising an adjustable frame and a mattress, to very complex (and expensive) structures incorporating many motors and moving parts. A number of common features or characteristics of conventional hospital beds lead to problems for patients. For example, typically only one option for movement is provided, namely raising or lowering of a back rest. Furthermore it is difficult for patients to move in the bed without assistance, and/or adjust the fixed features of the bed (such as armrests) that assist such movement. A further problem may be bedsores, which is a sore developed by a patient because of pressure caused by lying in a bed in one position (e.g., when the patient is unable to move themselves).

It is desired to provide an improved bed for use in a medical or therapeutic environment such as a hospital, as well as improved methods of controlling such beds.

SUMMARY

In an aspect of the present invention, which may be claimed independently, a support structure for a bed, comprising a plurality of sections, wherein each section is movable relative to the other sections and is configured to support a respective part of a body in use, and a plurality of resilient members that each extend in a longitudinal direction from an upper end of the bed to a lower end of the bed, wherein a shape and/or profile of the support structure corresponds to a shape and/or profile of the resilient members.

It has been found that using resilient members that each extend lengthwise along the bed from an upper end to a lower end of the bed, as described above, and when the bed is formed of a plurality of movable sections, improves the ability of the bed to conform to the shape of a body lying on the bed. Conventional beds that incorporate movable sections, but with resilient members that do not extend along the bed from an upper end to a lower end, are less able to conform to the shape of a body lying on the bed.

The shape and/or profile of the resilient members may substantially conform to the shape of a body, e.g., a human body and optionally in at least one configuration of the movable sections. The resilient members may have a wavy profile in the longitudinal direction, to allow them to easily conform to the shape of a body.

A shape and/or profile of each of the resilient members may change upon relative movement of the plurality of sections. Since the shape and/or profile of the support structure corresponds to the shape and/or profile of the resilient members, this means that the shape and/or profile of the support structure may be governed or controlled by movement of the plurality of sections and via the resilient members.

The plurality of sections may be separated from each other by a transverse separation line. The longitudinal direction may refer to the lengthwise or longest dimension of the support structure or bed, and references to transverse herein may refer to a direction perpendicular and transverse to the longitudinal direction. Each of the plurality of sections may be rotatable about a respective one of the transverse separation lines, and a shape and/or profile of each of the resilient members may change upon rotation of one or more of the plurality of sections.

The plurality of sections may comprise at least three sections, each corresponding to a respective part of a body in use. For example, a first of the plurality of sections may be configured to support an upper body portion, e.g., including a back and possibly also a head. A second of the plurality of sections may be configured to support an upper leg portion, e.g., above the knee. A third of the plurality of sections may be configured to support a lower leg portion, e.g., below the knee. The support structure may consist only of the first, second, and third sections referred to herein (i.e., optimised for a human body), or may comprise more sections if desired for a particular application. In some embodiments, the support structure may comprise just two sections.

In order to change the shape and/or profile of the support structure (and bed), in some embodiments a control system may be used to move at least one of the plurality of sections. This, in turn, causes the resilient members to change shape and/or profile, which as discussed above causes the shape and/or profile of the support structure (and bed) to change as well.

In any of the aspects or embodiments disclosed herein, each resilient member may be a single resilient member extending from the upper end of the bed to the lower end of the bed.

Each resilient member may be held in place, e.g., attached to or otherwise fixed in position, at each transverse separation line, which can allow the resilient members to change shape and/or profile as the plurality of sections move relative to each other.

The support structure may be movable between a first configuration and second configuration, wherein a shape or profile of the support structure in the first configuration is different to a shape or profile of the support structure in the second configuration.

The bed may be movable between the first configuration and the second configuration by relative movement of the plurality of sections.

The first configuration may correspond to a substantially flat or lying configuration, and the second configuration may correspond to an upright or seated configuration.

The support structure may further comprise a control system (e.g., the control system referred to above) configured to change a longitudinal profile of the resilient members so that the support structure moves between the first configuration and the second configuration.

A longitudinal profile of the support structure may corresponds to the longitudinal profile of the resilient members in a lengthwise direction along the bed throughout the movement of the bed from the first configuration to the second configuration. This can allow the resilient members to provide the ability to conform to the shape of a body lying on the bed throughout their range of motion.

The resilient members may be configured to exhibit at least one concave and/or convex portion in the longitudinal direction, which can allow them to easily conform to the shape of a body. In the flat configuration referred to above, it may be that the resilient members are also flat. However, in these embodiments it is desired that the resilient members exhibit at least one concave and/or convex portion in at least one configuration of the movable sections, e.g., in the upright or seated configuration.

The support structure may further comprise one or more sensors connected to one or more of the resilient members, and configured to determine one or more characteristics of the resilient members.

A control system (e.g., the control system referred to above) may be configured to monitor the one or more characteristics of the resilient members over time, via the one or more sensors, and output an alert or flag based on an analysis of the characteristic.

The control system may be configured to output an alert or flag if the characteristic (i) varies by more than a predetermined amount, (ii) remains outside a predetermined range of values, for a predetermined time, or (iii) remains within a predetermined range of values, for a predetermined time.

The one or more characteristics may comprise a tension and/or stiffness and/or strain of the resilient members.

In various embodiments, the resilient members may be configured to support a patient lying on the support structure, e.g., from head to toe. The resilient members may provide the primary support for a patient lying on the support structure. The shape and/or profile of the resilient members may be different in each of the plurality of sections.

The resilient members may be biased so as to form a predefined shape and/or profile upon movement of the plurality of sections of the support structure.

In an aspect of the present invention, there is provided a bed comprising a support structure as described above. The support structure may extend along the entire length of the bed, and or may define the length of the bed. The bed may comprise a mattress, and the mattress may form part of the support structure, e.g., may be integrated into the support structure, or the mattress may rest on top of the support structure and may be further attached or connected thereto to prevent the mattress moving relative to the support structure. The resilient members may be embedded into the mattress, or the mattress may rest on top of the resilient members.

In an aspect of the present invention, which may be claimed independently, there is provided a bed comprising a support structure configured to support a body in use, wherein the support structure comprises a plurality of resilient members (e.g., springs) that each extend lengthwise along the bed from an upper end of the bed to a lower end of the bed.

The bed may be movable between a flat configuration and a seated configuration. The resilient members may be configured to change shape upon movement of the bed between the flat configuration and the seated configuration. In the flat configuration the springs may substantially conform to the shape of a body in a lying position (or, less preferably, the springs may be substantially straight), and in the seated configuration the springs may conform substantially to the shape of the body in a seated position.

In the flat and/or the seated configuration the springs may comprise a concave profile (e.g., a pit or valley) at a centre portion of the bed, and a convex profile when moving from the centre portion to the upper and/or lower ends of the bed. The concavity and/or convexity of the springs may be more accentuated when the bed is in the seated position than when the bed is in the flat position.

The resilient members may be configured so that a longitudinal profile of the resilient members changes upon movement of the bed between the flat configuration and the seated configuration, for example to adapt to the changing posture or profile of a person on the bed. The longitudinal profile may be defined as or correspond to the contour of the springs in a lengthwise direction along the bed.

Each resilient member may be a single resilient member extending from the upper end of the bed to the lower end of the bed. The resilient members may be fixed in position at one or more spaced apart attachment locations (e.g., at least 3, 4 or 5 attachment locations). Between the attachment locations, which may be located at pivot points of the bed as described herein, the springs may be biased towards or away from a person lying on the bed. This can create a convex or concave portion of the bed in the longitudinal direction. It has been found that using resilient members that extend lengthwise along the bed from an upper end to a lower end, as described above, improves the ability of the bed to conform to the shape of a body, as the bed moves between flat and seated configurations.

In an aspect of the present invention, which may be claimed independently, there is provided an apparatus comprising a bed and a control system, wherein the bed is configured to support a body and is separated into one or more portions that each correspond to a specific part of the body, wherein each of the portions is movable so that the part of the body corresponding to each portion can be moved in a specified direction, and the control system is configured to move each of the one or more portions of the bed in their specified direction if and/or when the part of the body corresponding to that portion is moved. In other words, the control system may be configured to move each of the one or more portions of the bed in their specified direction in response to the part of the body corresponding to that section being moved.

The one or more portions may comprise a plurality of portions, and each portion may correspond to at least one of a limb, the upper body, the lower body and a shoulder.

The apparatus may further comprise one or more sensors configured to sense a current state (e.g., profile or posture) of the body, and/or when the part of the body corresponding to each portion is moved. Each portion may comprise its own sensor, and/or each sensor may be a pressure or other position sensor. The sensor may be a remote sensor (e.g., an infrared sensor). The control system may be configured to receive a notification from the sensor if the body is in or moves to a particular state (e.g., profile or posture), and/or if the part of the body corresponding to a particular portion is moved, and then optionally move one or more of the portions, or that particular portion respectively in its specified direction in response to the notification. The principle of this aspect of the invention is that the bed should amplify, rather than initiate the movement of the person on the bed, which can aid in their recovery and/or well-being.

In an aspect of the present invention, which may be claimed independently, there is provided an apparatus comprising a bed and a control system, wherein the bed is configured to support a body and is separated into one or more portions that each correspond to a specific part of the body, wherein each of the portions is movable so that the part of the body corresponding to each portion can be moved in a specified direction, and the control system is configured to store a routine for each of said one or more portions of the bed, wherein each routine corresponds to a movement of the bed in its specified direction for a certain number of repetitions, and to move each portion in its specified direction for the number of repetitions upon receiving a command.

In an aspect of the present invention, which is seen as novel and inventive in its own right and may, therefore, be claimed independently, there is provided an apparatus comprising a bed (e.g., the bed comprising resilient members referred to above) and a control system, wherein the bed is configured to support a body and is separated into one or more portions (e.g., the plurality of sections) that each correspond to a specific part of the body, wherein each of the portions is movable so that the part of the body corresponding to each portion can be moved in a specified direction, and the control system is configured to move one or more of the portions of the bed in their specified direction if and/or when a bedsore is detected, or (alternatively) upon detecting that the body has not moved for a certain (e.g., predefined or predetermined) amount of time.

The apparatus may further comprise one or more sensors (e.g., an array of pressure sensors) configured to detect pressure caused by the patient lying in the same position for a period of time (e.g., the predefined or predetermined amount of time). The sensors may be configured to notify the control system that a bedsore is detected, or is likely to develop, when the sensor detects that a patient has continuously applied a pressure to that sensor for a period of time, which pressure exceeds a threshold pressure.

In response, the control system may move one or more of the portions of the bed in their specified direction to alleviate the bedsore, or prevent it from occurring. The control system may decide which portions of the bed should be moved based on the location of the bedsore, or expected location of the bedsore (e.g., as detected by the sensor(s)).

For example, the control system may receive a notification that a bedsore is detected, or is likely to develop in the portion of the bed corresponding to the left leg. The control system may then determine that the portion of the bed corresponding to the left leg should be moved to alleviate the bedsore or prevent it from forming, and then move that portion of the bed. It will be appreciated that the bedsore may be alleviated by moving portions of the bed other than the one in which the bedsore was detected.

The control system may simply move the one or more of the portions of the bed in their specified direction if the patient has not moved for a period of time, e.g., the predefined or predetermined amount of time.

As such, the invention also provides a method of monitoring a patient on a bed (e.g., the bed comprising resilient members referred to above), the method comprising:

providing a bed configured to support a body and separated into one or more portions (e.g., the plurality of sections) that each correspond to a specific part of the body, wherein each of the portions is movable so that the part of the body corresponding to each portion can be moved in a specified direction;

monitoring one or more sensors associated with (e.g. connected to and/or within) the bed, wherein the one or more sensors are configured to detect that the body has not moved for a predefined or predetermined amount of time; and moving at least some of the one or more portions of the bed in their specified direction if and when the sensors detect that the body has not moved for the predefined or predetermined amount of time.

The control system may store data (e.g., in memory), including instructions for the control system to move a predetermined portion or portions of the bed in response to a bedsore being detected. This may depend on the type and/or location of the bedsore, for example a bedsore detected in a portion of the bed corresponding to the left leg may be alleviated by raising that portion of the bed. Alternatively, a bedsore detected in the lower back may be alleviated by raising the portion of the bed corresponding to both legs.

In an aspect of the present invention, which may be claimed independently, there is provided an apparatus comprising a support member for attachment to a bed, wherein the support member is switchable between a first, flexible state and a second, rigid state. In the first, flexible state the member may be movable by a user into a plurality of different shapes or positions. Upon switching to the second, rigid state the support member may be fixed and not movable by a user into a different shape or position.

In an aspect of the present invention, which may be claimed independently, there is provided a method of monitoring a person on a bed. A control system may be provided to monitor the person, and communicate with one or more of the sensors (as described herein) in respect of the monitoring.

Various embodiments of the present invention relate to the monitoring of a patient (or other user) when sitting or lying on a hospital bed. This is an important issue as conventional hospital beds have either inadequate monitoring systems, or are very complicated.

The aim of these embodiments is to have a control system that can reduce the burden on hospital staff (or other care workers) and also improve generally the monitoring systems currently in use.

BRIEF DESCRIPTION OF THE DRAWINGS

Various embodiments will now be described, by way of example only, and with reference to the accompanying drawings in which:

FIG. 1 shows a bed in accordance with one embodiment of this disclosure; and

DETAILED DESCRIPTION

Figure 2A:
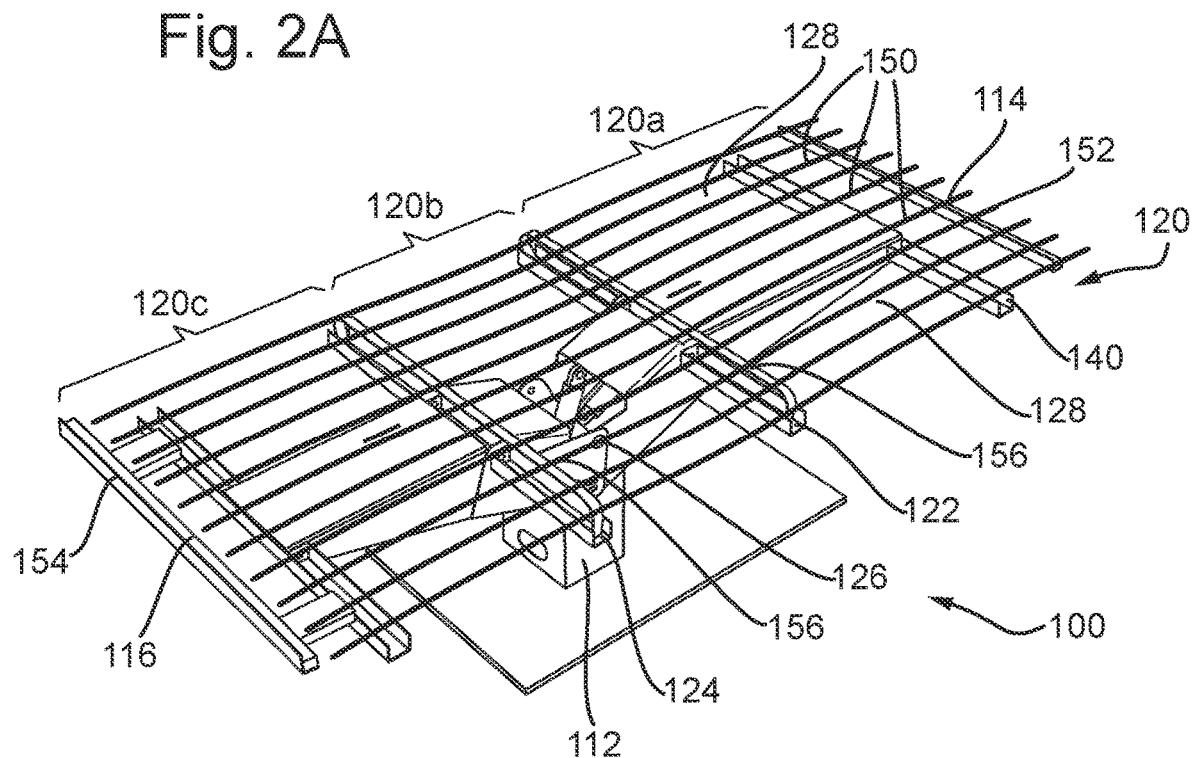
FIGS. 2A and 2B show a bed in accordance with another embodiment of this disclosure.

Various aspects of the present invention are directed to a bed, or a support structure for a bed. The bed may be a medical (e.g., hospital) bed upon which a patient lies, for example to recover from an illness or surgery.

Other applications for a bed as disclosed herein are contemplated, and any application that will make use of the disclosed improvements are intended to fall within the scope of the present disclosure even if not explicitly stated. For example, the bed is not limited to use in a hospital environment, but could be used, e.g., in a physiotherapy clinic to aid in recovery from certain injuries, or in a therapeutic environment.

Non-medical applications are also contemplated and intended to fall within the broadest aspects of the invention as described herein. As such, references to "patient" and "caregiver" herein are not intended to limit the embodiments to medical applications, and the terms "patient" and "caregiver" are interchangeable with any terms that refer to a person that might lie on, use or operate the bed as appropriate, for example "user", "controller" or "operator".

As used herein, the term "resilient" may refer to a material that is able to recoil (or spring) back into shape after bending, stretching, or being compressed.

The Bed and Support Structure

An example of a bed 10 is shown in FIG. 1 and the bed 10 may comprise a bed support 12 that may be adjustable, for example telescopic such that the bed support 12 can raise and/or lower a patient lying on the bed 10 by adjusting the bed support 12. The adjustment of the bed support 12 may be provided using a motor (not shown) or, less preferably, a manual device such as a lever.

The bed 10 may comprise an upper end 14 and a lower end 16. The upper end 14 may refer to the end of the bed 10 closest to or configured to support a patient's head, while the lower end 16 may refer to the end of the bed 10 closest to or configured to support a patient's legs or feet. The bed 10 may comprise wheels 18 to allow or assist movement of the bed 10.

The bed 10 may further comprise a support structure 20 for supporting a patient and/or adapting the shape of the bed in use. The support structure 20 may comprise a plurality of sections 20a, 20b, 20c, 20d. Four sections are shown in FIG. 1 although the present invention is not limited to the use of four sections. However, use of at least three sections has been found to be convenient since the body comprises two major points of flexure while lying down, namely at the knees and waist. In the embodiment of FIG. 1 a further (optional) point of flexure is provided for the neck. This will be described in more detail below.

The support structure 20 may comprise a first section 20a which preferably supports the head of a patient lying on the bed 10. The first section 20a may be rotatable or otherwise movable (e.g., up and down) such that the head of the patient may be raised and/or lowered. A motor (not shown) may be provided to rotate or raise/lower the first section 20a, for example about a first pivot point 22. Rotation or other movement of the first section 20a may act to raise and/or lower the head of a patient lying on the bed 10.

The support structure 20 may comprise a second section 20b which preferably supports the back of a patient lying on the bed 10. The second section 20b may be rotatable or otherwise movable (e.g., up and down) such that the upper body, torso or back of the patient may be raised and/or lowered. A motor (not shown) may be provided to rotate or raise/lower the second section 20b, for example about a second pivot point 24. Rotation or other movement of the second section 20b may act to raise and/or lower the upper body, torso or back of a patient lying on the bed 10.

The second section 20b may be connected to the first section 20a at the first pivot point 22, in such a manner that the first section 20a and the second section 20b may be free to rotate or otherwise move relative to each other, for example the first section 20a may be connected to the second section 20b via a hinge.

The support structure 20 may comprise a third section 20c which preferably supports the upper legs (e.g., the portion of the body between the knees and waist) of a patient lying on the bed 10. The third section 20c may be movable such that a concave portion 30 is created at the third section 20c. To achieve this a central pivot point 25 may be located generally in the middle of the third section 20c, and the support structure may be configured such that upper and lower halves of the third section 20c (which may be separated by the central pivot point 25) can be rotated towards each other to create the concave portion 30.

The third section 20c may be configured such that the upper legs of the patient may be raised and/or lowered by rotating or otherwise moving (e.g., raising or lowering) the lower half of the third section. A motor (not shown) may be provided to rotate or otherwise move the lower half of the third section 20c, for example about the central pivot point 25. Rotation of the lower half of the third section 20c may act to raise and/or lower the legs (and specifically the upper legs) of a patient lying on the bed 10.

The third section 20c may be connected to the second section 20b at the second pivot point 24, in such a manner that the second section 20b and the third section 20c may be free to rotate or otherwise move relative to each other, for example the second section 20b may be connected to the third section 20c via a hinge.

The support structure 20 may comprise a fourth section 20d which preferably supports the lower legs (e.g., the portion of the body below the knees, including the feet) of a patient lying on the bed 10. The fourth section 20d may be rotatable or otherwise movable (e.g., up and down) such that the lower legs of the patient may be raised and/or lowered. A motor (not shown) may be provided to rotate or raise/lower the fourth section 20d, for example about a third pivot point 26. Rotation or other movement of the fourth section 20d may act to raise and/or lower the legs (and specifically the lower legs) of a patient lying on the bed 10.

The fourth section 20d may be connected to the third section 20c at the third pivot point 26, in such a manner that the third section 20c and the fourth section 20d may be free to rotate or otherwise move relative to each other, for example the third section 20c may be connected to the fourth section 20d via a hinge.

Each of the plurality of sections 20a, 20b, 20c, 20d may be rotatable or movable and may be rotatable or movable independently of one another. A common motor may be provided and may be configured to rotate or move each of the sections 20a, 20b, 20c, 20d, or a plurality of motors may be provided, for example each section of the plurality of sections 20a, 20b, 20c, 20d may have a dedicated motor configured to rotate or move its respective section.

Each of the plurality of sections 20a, 20b, 20c, 20d may be connected to an adjacent section, for example via a hinge. The support structure 20 may, in this manner, be removable or replaceable as a single unit.

The support structure 20 may be movable as a single unit, for example the support structure 20, including all of the plurality of sections 20a, 20b, 20c, 20d may be movable as a single unit, e.g., the support structure 20 may be raised or lowered as a single unit, for example using the bed support 12. The support structure 20 may be rotatable as a single unit about the central pivot point 25, for example all of the plurality of sections 20a, 20b, 20c, 20d may be rotatable as a single unit about the central pivot point 25.

The support structure 20 may be configured to support the entire body of a human, for example an adult human from head to toe.

The support structure 20 may, therefore, have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure. The support structure 20 may extend along the entire length of the bed 10.

The support structure 20 may have a width equal to or greater than about 0.8 m, 0.9 m, about 1 m or about 1.1 m. The width may correspond to a direction perpendicular or transverse to the length.

The support structure 20 may be raised from the ground by a height of between about 0.1-1 m, about 0.2-0.9 m, about 0.3-0.9 m, or about 0.5-0.9 m.

The bed 10 may be adjustable such that a concave profile 30 (e.g., a pit or valley) may be created at a region of the bed, for example the third section 20c as described above, and/or a region of the bed 10 where a patient's buttocks rest, in use. This may be a central portion of the bed 10, although could be located slightly off centre. The central portion may be defined as being a position along the length of the bed 10 which is a distance that is about 0.35-0.65 times the length of the bed 10 or support structure 20 as measured from either the upper end 14 or the lower end 16 of the bed 10 or support structure 20.

For example, the concave profile 30 may be located at a position along the length of the bed which is a distance that is about 0.4-0.5 times the length of the bed 10 or support structure 20 as measured from the lower end 16 of the bed 10 or support structure 20.

A point of inflection 32 of the concave profile 30 may be located in this region, and in some embodiments the point of inflection 32 may be located at a position along the length of the bed which is a distance that is about 0.45 times the length of the bed 10 or support structure 20 as measured from the lower end 16 of the bed 10 or support structure 20.

The length of the bed 10 may be taken as the length of the support structure 20, for example made up of the lengths of each of the sections 20a, 20b, 20c, 20d of the support structure 20.

The concave profile 30 may be created by rotating two sections of the bed (e.g., the upper and lower halves of the third section 20c) such that a concavity or an obtuse angle is formed between the two sections. In the illustrated embodiment of FIG. 1, for example, a concave profile 30 is created by rotating the upper and lower halves of the third section 20c of the support structure 20 accordingly, such that a concavity or an obtuse angle is formed between them.

The concave profile 30 can prevent a patient slipping down the bed 10 in use, in that one of the sections forming the concave profile 30 (e.g., the third section 20c) may resist the movement of a patient in a certain direction.

In some embodiments one or more sections of the support structure 20 may be configured to support the legs (e.g., the lower half of the third section 20c and/or fourth section 20d in FIG. 1), for example the upper legs. This section may be configured such that it can be rotated above the horizontal (e.g., a horizontal line parallel with the ground) in order to resist the movement of a patient, for example movement towards the lower end 16 of the bed 10. This can be helpful in preventing slippage of the patient, for example when the patient raises the sections of the bed supporting the back and/or head (e.g., the first section 20a and/or the second section 20b), e.g., when sitting up.

As described above and in reference to the example of FIG. 1, the support structure 20 may comprise two (or at least two) pivot points 24, 26, corresponding to two points of flexure of a human while lying down, namely at the knees and waist. A further pivot point 22 may be provided corresponding to a third point of flexure, for example the neck. Each of the plurality of sections 20a, 20b, 20c, 20d of the support structure 20 may be configured to rotate about a pivot point 22, 24, 25, 26.

A first 22 of the pivot points may be located approximately at the location a patient's neck or shoulders rest on the bed 10, for example a position along the length of the bed 10 which is a distance that is about 0.10-0.35, about 0.10-0.25, about 0.10-0.20, about 0.10-0.15 or about 0.125 times the length of the bed 10 or support structure 20 as measured from the upper end 14 of the bed 10 or support structure 20.

A second 24 of the pivot points may be located approximately at the location a patient's waist rests on the bed 10, for example a position along the length of the bed 10 which is a distance that is about 0.35-0.65, about 0.35-0.55, about 0.40-0.45 or about 0.425 times the length of the bed 10 or support structure 20 as measured from the upper end 14 of the bed 10 or support structure 20.

A third 26 of the pivot points may be located approximately at the location a patient's knees rest on the bed 10, for example a position along the length of the bed 10 which is a distance that is about 0.65-0.90, about 0.75-0.90, about 0.80-0.90, about 0.85-0.90 or about 0.875 times the length of the bed 10 or support structure 20 as measured from the upper end 16 of the bed 10 or support structure 20.

It will be appreciated that these dimensions could vary in the disclosed ranges due to the shape of the bed 10 or support structure 20. It is assumed that the bed 10 and/or support structure 20 roughly match the length of a human body, with possibly a gap at the top and bottom to take account of the varying size of different people. The length of the bed 10 or support structure 20 may be the lengthwise or longest dimension of the bed 10 or support structure 20.

The pivot points 22, 24, 25, 26 may be lateral pivot points and the axis of rotation of the pivot points (and the respective sections that rotate about the pivot points) may be transverse to the lengthwise dimension of the bed 10.

Further movement of the bed 10 about other axes of rotation are envisaged within the broadest aspects of this disclosure.

For example, one or more of the sections 20a, 20b, 20c, 20d may be additionally rotatable about one or more axes of rotation that are not transverse to the longitudinal direction of the bed 10 (i.e., an axis of rotation having a longitudinal component), for example an axis of rotation that is at an angle with respect to the transverse direction, wherein the angle may be selected from the group consisting of: (i) 0°-10°; (ii) 10°-20°; (iii) 20°-30°; (iv) 30°-40°; (v) 40°-50°; (vi) 50°-60°; (vii) 60°-70° (viii) 70°-80°; and (iv) 80°-90°. The one or more additional axes of rotation may be substantially in line with the longitudinal direction, or normal to the transverse direction.

The one or more additional axes of rotation may be provided, for example, so that the patient can perform movements that are not possible by rotating the bed around a transverse axis of rotation.

The support structure 20 may be configured to rotate a single limb or body part of a patient, whilst optionally keeping the remaining limbs or body parts substantially stationary. For example, the support structure 20 may be configured to raise a shoulder independently of the other shoulder, so as to perform a twisting motion of the body. Such an exercise can aid in recovery of a specific injury to one shoulder, for example.

In order to do this the first section 20a and/or the second section 20b of the support structure 20 may be rotatable about an axis of rotation having a longitudinal component, for example an axis of rotation that is at an angle with respect to the transverse direction, wherein the angle may be selected from the group consisting of: (i) 0°-10°; (ii) 10°-20°; (iii) 20°-30°; (iv) 30°-40°; (v) 40°-50°; (vi) 50°-60°; (vii) 60°-70° (viii) 70°-80°; and (iv) 80°-90°.

Such a movement may be effectuated using an additional hinge located at the second transverse pivot point 22, for example, that allows part of the first section 20*a* and/or the second section 20*b* to rotate about the axis of rotation having a longitudinal component.

One or more of the sections 20*a*, 20*b*, 20*c*, 20*d* may be split longitudinally into two sub-sections, for example along a line that is approximately coaxial with a central, longitudinal axis of the bed 10. Each of the sub-sections may be rotatable with the transverse rotation of the section as a whole, but also independently rotatable about a different axis of rotation, for example about an axis of rotation having a longitudinal component, for example an axis of rotation that is at an angle with respect to the transverse direction, wherein the angle may be selected from the group consisting of: (i) 0°-10°; (ii) 10°-20°; (iii) 20°-30°; (iv) 30°-40°; (v) 40°-50°; (vi) 50°-60°; (vii) 60°-70° (viii) 70°-80°; and (iv) 80°-90°. The axis of rotation of the sub-sections may be approximately normal to the transverse axis of rotation.

The independent rotation of the sub-sections may be achieved through the use of one or more hinges located at the pivot point(s) of the support structure 20, or any other suitable mechanism.

In various embodiments, the support structure 20 may comprise a plurality of sections (e.g., at least three sections and/or similar to the sections 20*a*, 20*b*, 20*c*, 20*d*), and all or part of the sections may be movable by a translating means, e.g., other than rotation about a pivot point. For example, each section may be movable (e.g., up and down) independently of the other sections. Additionally, or alternatively, a portion of each section may be movable (e.g., up and down) independently of the rest of the section, and/or independently of the other sections.

The support structure 20 may comprise or form part of a mattress upon which a patient rests in use. Alternatively a mattress may be separate to the support structure 20 and attached to or rested on the support structure 20.

The Mattress

As discussed above the bed may comprise a mattress and the mattress may form part of the support structure (e.g., be integrated into the support structure) or the mattress may rest on top of the support structure and may further be attached or connected thereto to prevent the mattress moving (e.g., slipping) relative to the support structure.

An example of an integrated mattress and support structure 120 will now be described with reference to FIGS. 2A-2B.

The support structure 120 may form part of a bed 100 and is similar to that shown and described above in respect of FIG. 1. The support structure 120 comprises a plurality of sections 120*a*, 120*b*, 120*c* each configured to support a respective part of a patient's body. In the illustrated embodiment of FIG. 2A a first section 120*a* is configured to support a patient's upper body, including the back and head, a second section 120*b* is configured to support a patient's upper legs, and a third section 120*c* is configured to support a patient's lower legs.

The first section 120*a* may have a length of between about 0.7-1.1 m, optionally about 0.8 m. The second section 120*b* may have a length of between about 0.4-0.5 m, optionally about 0.45 m. The third section 120*c* may have a length of between about 0.5-0.6 m, optionally about 0.55 m. The length may correspond to the lengthwise or longest dimension of the support structure 120. The support structure 120 may extend along the entire length of the bed 100.

As with the embodiment of FIG. 1, each section may be separated from an adjacent section by a transverse separation line (e.g., a pivot point) 122, 124. A first separation line 122 may separate the first section 120*a* from the second section 120*b*, and a second separation line 124 may separate the second section 120*b* from the third section 120*c*. The first and second separation lines 122, 124 may correspond to the major points of flexure of a human, as discussed above, namely the knees and waist. A crossbeam or lateral support bar may be located at each of the first and second separation lines 122, 124.

A central pivot point 126 may be located at approximately the centre of the bed 10, for example at the point at which a bed support 112 meets the support structure 120, such that the support structure 20 of the bed 10 can rotate as a whole about the central pivot point 126. The central pivot point 126 may not necessarily be located at a point of flexure, and/or may be located at a point between the first and second separation lines 122, 124.

The support structure 120 may have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure. The support structure 120 may extend along the entire length of the bed 100.

The support structure 120 may have a width equal to or greater than about 0.8 m, 0.9 m, about 1 m or about 1.1 m. The width may correspond to a direction perpendicular or transverse to the length.

The support structure 120 may be raised from the ground by a height of between about 0.1-1 m, about 0.2-0.9 m, about 0.3-0.9 m, or about 0.5-0.9 m.

The mattress may comprise a plurality of resilient members 150, for example springs that may extend in the longitudinal (i.e., lengthwise or longest) direction from an upper end 114 of the support structure 120 to a lower end 116 of the support structure 120. The resilient members 150 may be held in place at (e.g., attached to) the upper end 114 by an upper holding member 152, and at the lower end 116 by a lower holding member 154. For example, the resilient members 150 may be attached or connected (e.g., welded) to the upper and lower holding members 152, 154.

The resilient members 150 may be attached to further holding members 156 at each separation line. For example, the resilient members 150 may be attached or connected (e.g., welded) to the further holding members 156, for example to the crossbeams or lateral support bars that are located there (if provided).

The resilient members 150 may be configured to support a patient lying on the support structure 120 and/or may provide the primary support for a patient. While it is envisaged that a further material (e.g., foam or memory foam, which is not shown in FIGS. 2A-2B) may encase the resilient members 150, the shape and/or profile of the mattress may be determined by the shape and/or profile of the resilient members 150, as shown in more detail in FIG. 2B.

The various sections of the support structure 120 may be independently movable (e.g., up and down) and/or rotatable about their respective separation lines 122, 124. As the various sections of the support structure 120 rotate the resilient members 150 may be configured to change shape. In other words, the resilient members 150 may be biased so as to form a predefined shape and/or profile upon rotation of the various sections of the support structure 120. The shape and/or profile of the resilient members 150 (and therefore the mattress) may be different in each section.

Figure 2B:
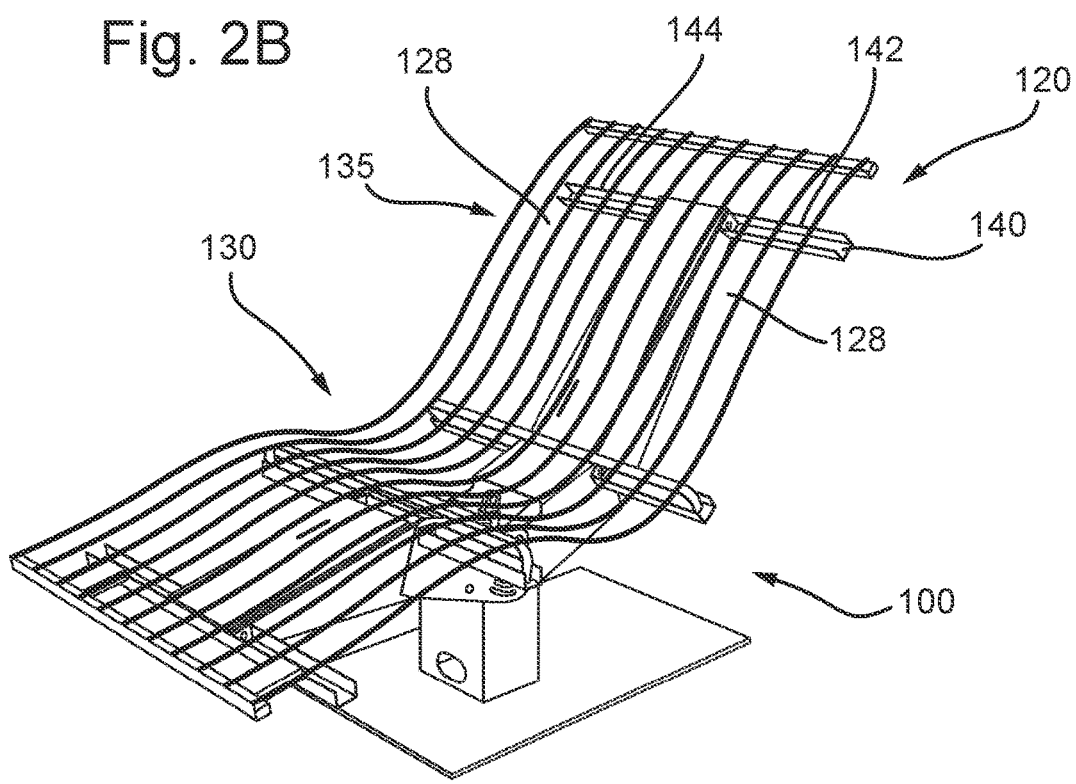

As shown in the illustrated embodiment of FIG. 2B, upon rotation of the first section 120*a* about the first separation line 122, and/or the third section 120*c* about the second separation line 124, the resilient members 150 may be configured to form a convex profile in the first section 120*a* and/or the third section 120*c* respectively, and may be configured to form a concave profile in the second section 120*b*.

References to "concave" and "convex" as used herein should be interpreted as being towards a person (e.g., patient) lying on the bed and in the longitudinal direction, for example such that a concave profile forms a depressed portion (e.g., a dip or valley) of the bed in a longitudinal direction, and a convex profile forms a raised portion (e.g., a bump or protrusion) of the bed in a longitudinal direction.

For example, upon rotation of the sections 120*a* and 120*b* from a flat position (as shown in FIG. 2A) into a more upright position (as shown in FIG. 2B) the support structure 120 automatically provides a concave profile 130 (e.g., a pit or valley) as well as a convex profile 135 for lumbar support. The use of longitudinal resilient members 150 (as opposed to vertical springs or lateral members) allows such profiling to be more easily tailored for an intended use of the bed.

The resilient members 150 may be configured, in the flat and upright positions of the support structure 120, to substantially conform to the shape of the body. For example, when the support structure 120 is in a flat position the resilient members 150 may preferably undulate to follow the contour of a body in a lying down position, or less preferably the resilient members 150 may be flat. When the support structure 120 is in an upright position, the support structure 120 may undulate to follow the contour of a body in a seated position. It will be appreciated that the undulations in the resilient members 150 when the support structure 120 is in the seated position may be more pronounced than the undulations in the resilient members 150 when the support structure 120 is in the flat position.

There may be no lateral resilient members or springs provided in the support structure 120. The resilient members 150 may have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure.

The support structure 120 may comprise at least 5, 10, 15 or 20 resilient members 150 and/or the resilient members may be spaced apart by less than 5, 10, 15 or 20 cm, to provide sufficient support to a person lying on the bed 100.

In various embodiments one or more sensors (not shown) may be connected to one or more (or all of) the resilient members 150, for example to ascertain information about the patient therefrom. For example, the tension in each resilient member 150 could be monitored by a control system. If it becomes apparent that the patient is moving towards the side of the bed, for example the tension in a central resilient member is reducing and the tension in an outer resilient member is increasing, the control system may determine that the patient is about to fall off the bed. The control system may then be configured to sound an alarm or otherwise alert a caregiver (or other person) prior to the patient actually falling off the bed. In embodiments where the bed comprises one or more movable portions, the control system may move (e.g., raise) a suitable portion of the bed in order to prevent the person falling off. This is an improvement over many conventional arrangements that provide an alert once the patient has fallen off the bed, but not beforehand.

The tension in the resilient members 150 could be monitored over time by the control system. Based on the change in the tension in the resilient members 150 over time the control system may determine movement patterns of the patient, some of which may lead to an alert. For example, if the tension is substantially stable then the control system may determine that the patient is moving normally and continue monitoring. If the tension varies by more than a predetermined amount (e.g., due to the patient thrashing or writhing) then the control system could sound an alarm or otherwise alert a caregiver (or other person). The use of sensors connected to the springs of the support structure 120 is seen as an improvement over conventional methods, in that it can more accurately track the movement of the patient. For example, the springs may extend along the entire length of the bed and can, therefore, sense an increased amount of movement of the person on the bed.

Various parts of the support structure 120 may be movable or rotatable in order to provide further automated movement possibilities for a patient, in addition to the rotation about the first and second separation lines 122, 124, and/or the central pivot point 126.

For example, the upper corners 128 of the support structure 120 may be adjustable such that they can be raised or lowered independently of each other and/or the other parts of the support structure 120. This can provide a movement configured to lift the shoulder of a patient lying on the bed.

To effectuate such movement a support bar 140 may be located at or near the upper end 114 of the support structure 120. The support bar 140 may comprise a left arm 142 and a right arm 144, both of which may be independently raised or lowered. One or more motors (not shown) may be provided to raise and lower each of the left arm 142 and right arm 144.

A similar arrangement may be placed at the lower end 116 of the support structure 120 in order to raise and lower the legs or feet of a patient lying on the bed.

Other movements are envisaged. The support structure 120 may be configured such that it can be raised and/or lowered about a longitudinal axis of rotation, for example the central longitudinal axis of the support structure 120. For example, each separation line may comprise a support bar similar to the support bar 140, wherein the support bars may be configured to simultaneously raise all of the right or left arms, so that one half of the support structure 120 is raised. Such a movement may assist in turning a patient.

In various embodiments, the support structure 120 may comprise a plurality of sections (e.g., at least three sections and/or similar to the sections 120*a*, 120*b*, 120*c*), and all or part of the sections may be movable by a translating means, e.g., other than rotation about a pivot point. For example, each section may be movable (e.g., up and down) independently of the other sections. Additionally, or alternatively, a portion of each section may be movable (e.g., up and down) independently of the rest of the section, and/or independently of the other sections.

The portion of each section may be independently movable by configuring the resilient members 150 such that each resilient member 150 is independently movable within that portion of the section. For example, separate actuators could be provided for each resilient member 150 that may be configured to move the resilient member 150 up and down within a particular section, or within a portion of a particular section.

Amplified or Assisted Movement

A further aspect of the present invention will now be described, and can be combined with any of the aspects or embodiments of a bed disclosed herein.

A method is disclosed that comprises providing a bed upon which a human or animal lies, in use, for example a medical (e.g., hospital) bed. The bed may be separated into one or more portions that each correspond to a specific part of the body, for example a limb such as a leg or arm, a shoulder, the torso or lower body, etc. The bed may be a bed as shown and described above in respect of FIG. 1, or FIGS. 2A-2B.

The bed may be configured such that each of the portions may be movable, so that the part of the body corresponding to each portion can be moved in a specified direction, for example to allow a patient lying on the bed to sit up, or perform an exercise such as a shoulder movement or leg raise. In various embodiments the movement may be to alleviate bedsores.

A control system may be provided and may be configured to move the portion of the bed in its specified direction if and/or when the specific part of the body corresponding to that portion is moved.

Additionally, or alternatively, the control system may be configured to amplify the movement of a part of the body by moving the portion of the bed corresponding to that part of the body in its specified direction, for example after detecting movement of that part of the body, which movement may be in the specified direction.

This is in contrast to conventional arrangements, which typically employ a control panel (or similar) in order to move a part of the body (e.g., sit up), but do not effectuate movement of the bed in response to movement of the patient. The principle of this aspect of the invention is that the bed should amplify, rather than initiate the movement of a patient.

It will be appreciated that not all movements of a patient would want to be amplified, or indeed that amplification, as opposed to initiation of movement is desired all the time. The control system may be switchable such that a patient or caregiver can turn on and off the function of amplified movement. For example, if a patient wants to sit up, but is not fit or well enough to use the amplified movement then the control system may be switched off. The patient can then use conventional controls to cause the bed to raise the upper body. However, if the patient would like to sit up with the amplified movement, the control system may be switched on. This means that the movement of the patient becomes the cause of the movement of the bed.

The control system may only effectuate movement of the bed after a given period of time has passed since the patient moved the body part in question. This can be made short enough to prevent unwanted fatigue, but long enough to prevent unnecessary or undesired movement of the bed, for example in response to a spasm. This function may not always be necessary, for example for certain movements or if the control system is switchable as described above.

The control system may include a switch configured such that the amplified movement can only be activated by the control system if the switch is depressed or otherwise activated. For example, a button may be provided on the bed, and the control system may only carry out the amplified movement if the button is depressed. Other types of switch may be used, such as a voice activated switch, or a switch that is controlled by a specific movement (e.g., an arm motion or eye movement). This would help avoid unwanted movements, and could be used in addition, or alternatively to the other methods of avoiding unwanted movements described herein.

Varying degrees of assistance may be provided. It is recognised that some patients may need more assistance than others. The control system may include one or more assistance factors that can be set by a user (e.g., the patient or a nurse/caregiver). The assistance factors may range from, e.g., 0-1, where 0 corresponds to no or minimum assistance and 1 corresponds to full or maximum assistance. The factor may increase from 0-1, for example in a linear fashion.

The control system may vary the power used to move the portion of the bed in its specified direction based on (e.g., in proportion to) one of the assistance factors, for example the higher the assistance factor the more power may be applied to move the portion of the bed, and vice-versa.

The control system may also vary the response time of the movement based on one of the assistance factors. The response time may refer to the time taken for the control system to effectuate movement of the portion of the bed in question, once the patient starts to move or initiates a movement. For a high assistance factor the control system may use or apply a shorter response time, and for a low assistance factor the control system may use or apply a longer response time.

It will also be appreciated that certain exercises may be possible. The control system may store a routine (e.g., in a memory device) and this may correspond to the part of the body corresponding to the portion of the bed in question, for example a leg. The control system may be configured to amplify the movement of the body part (e.g., leg) once it starts to move. The control system may be configured to do this for a set number of repetitions, and/or for multiple body parts (and multiple corresponding portions of the bed, such as each leg, or upper body and lower body, consecutively.

The one or more portions of the bed may correspond to portions of the bed that are configured to support certain parts of a patient's body in use. As discussed above the bed may be a bed as shown and described above in respect of FIG. 1, or FIGS. 2A-2B, in which case each portion of the bed may correspond to a section or sub-section of the bed or support structure as described above, wherein movement of the portions may be effectuated in the same manner as described above.

One or more motors may be provided to move the portions of the bed in the specified directions, which motors may be controlled by the control system. The control system may comprise a memory and a processor, wherein the memory stores data relating to the movements of the bed and the processor is configured to carry out the control steps described above in relation to the control system.

The portions of the bed may overlap one another. For example, first and second portions of the bed may be configured to support the upper and lower body of a patient lying on the bed, respectively. A third portion of the bed may be configured to support a right shoulder or arm of the patient, and a fourth portion of the bed may be configured to support a left shoulder or arm of the patient. The third and fourth portions may, therefore, be located within (and may form part or all of) the first portion. A similar arrangement may be created in the second portion by dividing this into fifth and sixth portions. Thus, the bed may be divided into quadrants, where the upper and lower halves of the bed may be movable as well as each quadrant.

Each portion of the bed may be independently movable, for example using one or more motors (not shown). Each portion of the bed may have a dedicated motor, or one or more switches may be configured to switch the transmission of one of the motors from one portion of the bed to another.

In an additional, related aspect a method is disclosed that comprises providing a bed upon which a person lies, for example a medical (e.g., hospital) bed. The bed may be separated into one or more portions that each correspond to a specific part of the body, for example a limb such as a leg or arm, a shoulder, the torso or lower body, etc.

The bed may be configured such that each of the portions may be movable, so that the part of the body corresponding to each portion can be moved in a specified direction, for example to allow a patient lying on the bed to sit up, or perform an exercise such as a shoulder movement or leg raise.

A control system may be configured to store a routine (e.g., in a memory device) and this may correspond to the part of the body corresponding to the portion of the bed in question, for example a leg. The control system may be configured to move the portion of the bed in question (e.g., raise and lower the portion) a certain number of repetitions. The number of repetitions may be stored in a memory of the control system, and/or may predetermined or set by a user (e.g., a caregiver).

The bed may be similar to the bed described above in respect of the amplified movement, although this aspect of the invention is related to the use of a moving bed that is divided into portions to provide dedicated and/or focused exercises, rather than amplified movement.

Instead of (or additionally to) the control system being configured to store a routine, the control system may be configured to move one or more of the portions of the bed in its specified direction if and/or when a bedsore is detected or predicted.

The bedsore may be detected or predicted through the use of one or more sensors at each portion (e.g., an array of sensors, optionally spread uniformly across the bed), which sensors may be configured to detect pressure or movement, for example pressure caused by the patient lying in one position for an extended period of time, or a lack of movement. For example, the sensor may be configured to detect when a patient has not moved a particular part of their body (and/or their body as a whole) for a period of time (e.g., a predefined or predetermined period of time), and notify the control system accordingly.

In response, the control system may move a selected portion or portions of the bed in its or their specified direction to alleviate the bedsore, or prevent it from occurring. The portion or portions moved may correspond to or at least include portions of the bed in which the most pressure was applied by the patient's body during the period of time, and/or other portions of the bed. The period of time (e.g., the predefined or predetermined period of time) may be a period longer than 30, 60, 120, 240 or 480 minutes. In addition, or alternatively, the period of time (e.g., the predefined or predetermined period of time) may be a period shorter than 480, 240, 120 or 60 minutes. In some embodiments, the period of time (e.g., the predefined or predetermined period of time) may be a period between about 30-480 minutes, optionally 60-240 minutes or further optionally 60-120 minutes.

The control system may store data (e.g., in memory), including instructions for the control system to move a predetermined portion or portions of the bed in response to a bedsore being detected or predicted. This may depend on the type and/or location of the bedsore or pressure points detected, for example a bedsore or pressure point detected in a portion of the bed corresponding to the left leg may be alleviated by raising or otherwise moving that portion of the bed. Alternatively, a bedsore or pressure point detected in the lower back may be alleviated by raising or otherwise moving the portion of the bed corresponding to both legs. A "pressure point" may be a location of heightened pressure with respect to the rest of the bed, as detected by the sensors (e.g., an array of sensors, such as pressure sensors) referred to above.

The control system may, alternatively or additionally to the above methods (and in an aspect of the invention independently claimable in its own right) move the one or more of the portions of the bed in their specified direction if the patient has not moved for a period of time, e.g., the predefined or predetermined amount of time. As such, the invention also provides a method of monitoring a patient on a bed or support structure (e.g., a bed or support structure as shown and described in respect of FIG. 1 or FIGS. 2A, 2B). This method comprises providing a bed or support structure configured to support a body and separated into one or more portions (e.g., the plurality of sections of FIG. 1 or FIGS. 2A, 2B) that each correspond to a specific part of the body, wherein each of the portions is movable so that the part of the body corresponding to each portion can be moved in a specified direction, monitoring one or more sensors associated with (e.g. connected to and/or within) the bed, wherein the one or more sensors are configured to detect that the body has not moved for a predefined or predetermined amount of time, and moving at least some (or all) of the one or more portions of the bed in their specified direction if and when the sensors detect that the body has not moved for the predefined or predetermined amount of time.

The predefined or predetermined period of time may be a period longer than 30, 60, 120, 240 or 480 minutes. In addition, or alternatively, the predefined or predetermined period of time may be a period shorter than 480, 240, 120 or 60 minutes. In some embodiments, the predefined or predetermined period of time may be a period between about 30-480 minutes, optionally 60-240 minutes or further optionally 60-120 minutes.

Again, the bed may be similar to the bed described above in respect of the amplified movement and/or to provide dedicated and/or focused exercises.

References to "concave" and "convex" as used herein should be interpreted as being towards a person (e.g., patient) lying on the bed and in the longitudinal direction, for example such that a concave profile forms a depressed portion (e.g., a dip or valley) of the bed in the longitudinal direction, and a convex profile forms a raised portion (e.g., a bump or protrusion) of the bed in the longitudinal direction.

Bedside Support Member

A further aspect of the present invention will now be described, and can be combined with any of the aspects or embodiments of a bed disclosed herein.

An apparatus is disclosed and comprises a member for attachment to a bed. The member may be attachable to the side of a bed, and may extend along the side of the bed, for example to prevent a patient falling out of the bed and/or may extend over the bed to provide a support beam, for example to assist in raising and lowering a patient lying on the bed. The bed may be a bed as shown and described above in respect of FIG. 1, or FIGS. 2A-2B.

The member may be movable between a first position, for example in which the member extends along the side of the bed to prevent a patient falling out of the bed, and a second (different) position, for example in which the member extends over the bed, e.g., to provide support for the patient or a caregiver.

In a first state the member may be flexible, and in a second state the member may be rigid. The member may be switchable between the first and second states, so that the member could be moved or manipulated into a position whilst in the first, flexible state and then fixed in that position by switching to the second, rigid state. This allows the member to be manipulated into a variety of different positions by a patient or caregiver. As used herein, "flexible" may mean that the member can be manipulated by a user, so as to form different shapes, and "rigid" may mean that the member, or a portion thereof is substantially fixed in position and cannot be manipulated by a user.

For example, the member may be fixed in a first position whilst in the second, rigid state, then switched to the flexible state and moved or manipulated into a second, different position, and then fixed in the second position by switching the member back to its second, rigid state. This process could be repeated many times depending on the needs of the patient or caregiver.

In this manner the member may convert from a safety item, e.g., preventing the patient from rolling out of the bed, to a support mechanism, e.g., to assist movement or help a patient when measuring blood pressure. Additionally, or alternatively the shape of the member can be altered in any direction, for example to assist in patient rehabilitation.

Figure 3A:
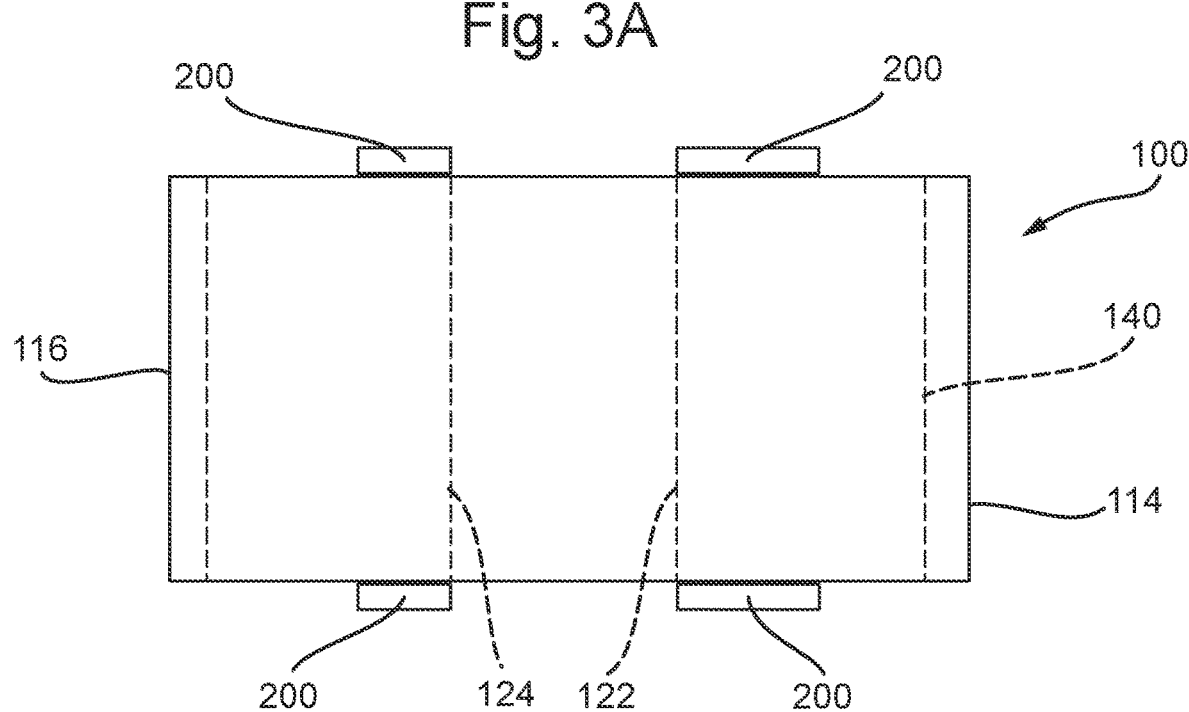
FIGS. 3A and 3B show examples of a support member attached to a bed in accordance with various embodiments of this disclosure.
Figure 3B:
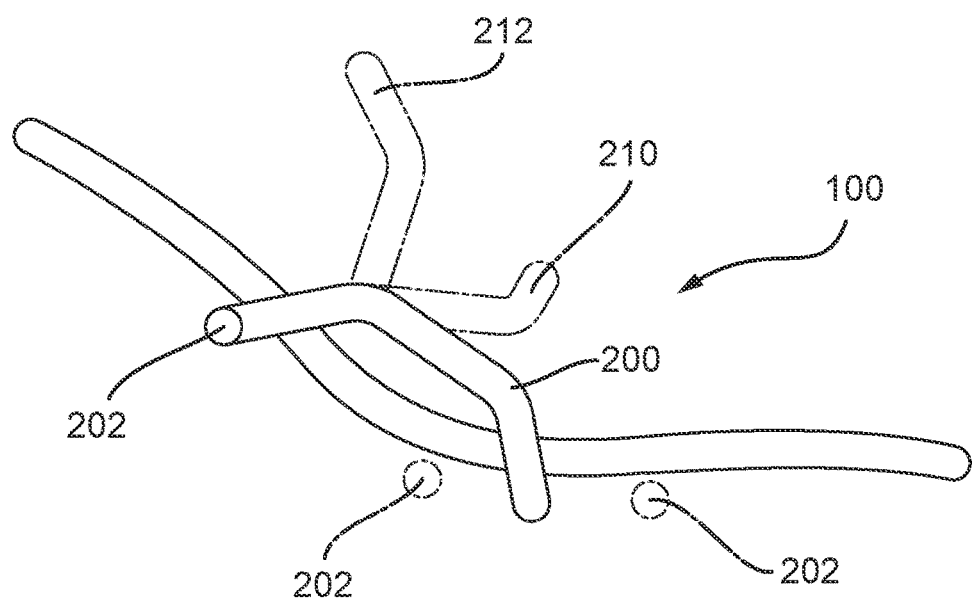

FIGS. 3A and 3B illustrate schematically how one or more members 200, each having the features of a member as described above, may be positioned and fixed with respect to a bed 100 (in this case the bed 100 is a bed as shown and described in respect of FIGS. 2A and 2B).

The one or more members 200 may be attached to the bed 100 such that at least a portion of the member 200 is located at or adjacent to the separation lines 122, 124, although they could be placed at any location along the side of the bed 100. Any number of members 200 could be placed along the side of the bed, although a particularly suitable area would be at or adjacent to the first separation line 122, as that is generally at the waist of a patient (where the hands are likely to be located).

In the embodiment of FIG. 3B, a single member 200 is provided, having the features of a member as described above, and is attached to the bed 100 at an attachment location 202. Further attachment locations 202 may be provided so that the member 200 can be moved between the attachment locations 202, or additional members 200 (not shown) could be attached to the bed 100 at these locations.

The attachment member 200 is shown in FIG. 3B with a solid line, to indicate a first position in which the member 200 extends along the side of the bed, wherein a portion of the member 200 is raised above the level of the mattress so as to prevent a patient falling out of the bed.

FIG. 3B also shows alternative positions 210, 212 of the member 200 in dashed lines, wherein the member 200 may be moved to a position 210 in which the member extends laterally across the bed 100, to provide a platform or support in a lateral direction. Alternatively, the member 200 could be moved to a position 212 in which the member 200 is raised substantially above the patient's head, so that, for example, the patient can use the member 200 to lift themselves up.

As discussed above, and generally, the member may be able to transition between a flexible and rigid state and a number of mechanisms are envisaged to enable this.

Figure 3C:
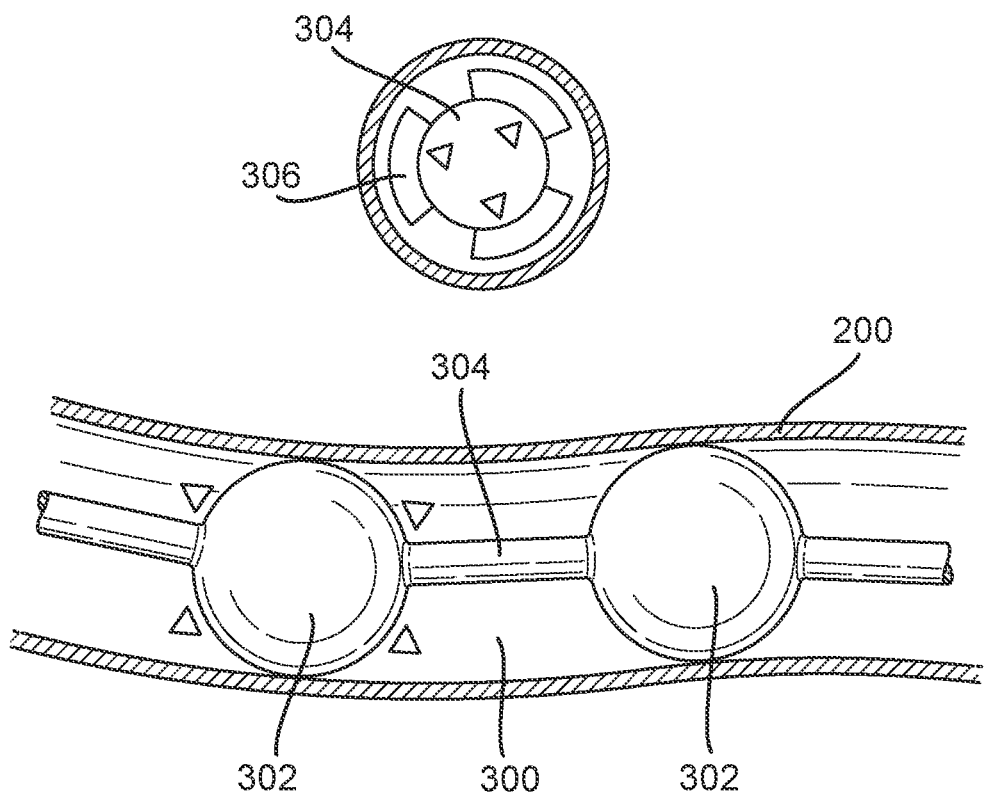
FIGS. 3C-3G show examples of types of support member in accordance with the embodiments of 3A and 3B.

FIG. 3C shows a system in which the member may be formed using a hollow tube 300, which may be made from neoprene, within which is held a series of expandable balls 302 connected by a fluid-carrying tube 304. The fluid in the fluid carrying tube 304 may be selectively pressurised (for example using a control system), at which point the balls expand and lock in position. For example, the increased pressure may urge elements 306 located initially on or within the balls towards the inner surface of the tube 300.

This can cause the member 200 to become substantially rigid, and the member will be in its second, rigid state. Upon depressurisation of the fluid in the fluid carrying tube 304 the balls may contract (e.g., the elements 306 may detract and no longer be urged towards the inner surface of the tube 300), so that the member 200 will be in its first, flexible state.

Figure 3D:
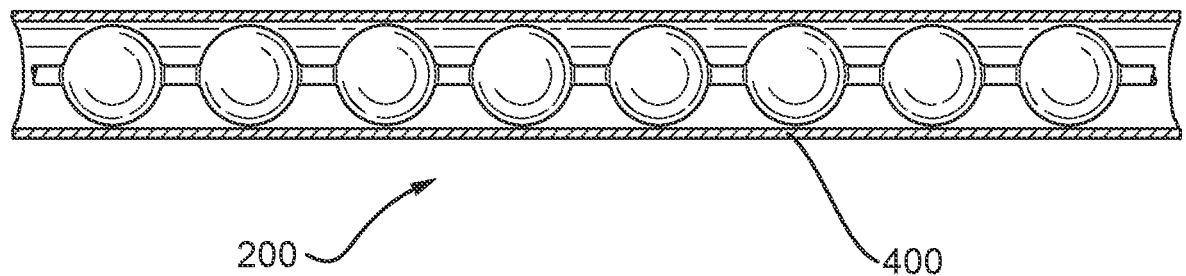

FIG. 3D depicts a further embodiment of the member 200 in which the member 200 is formed by a tube 400 having a series of pockets.

Figure 3E:
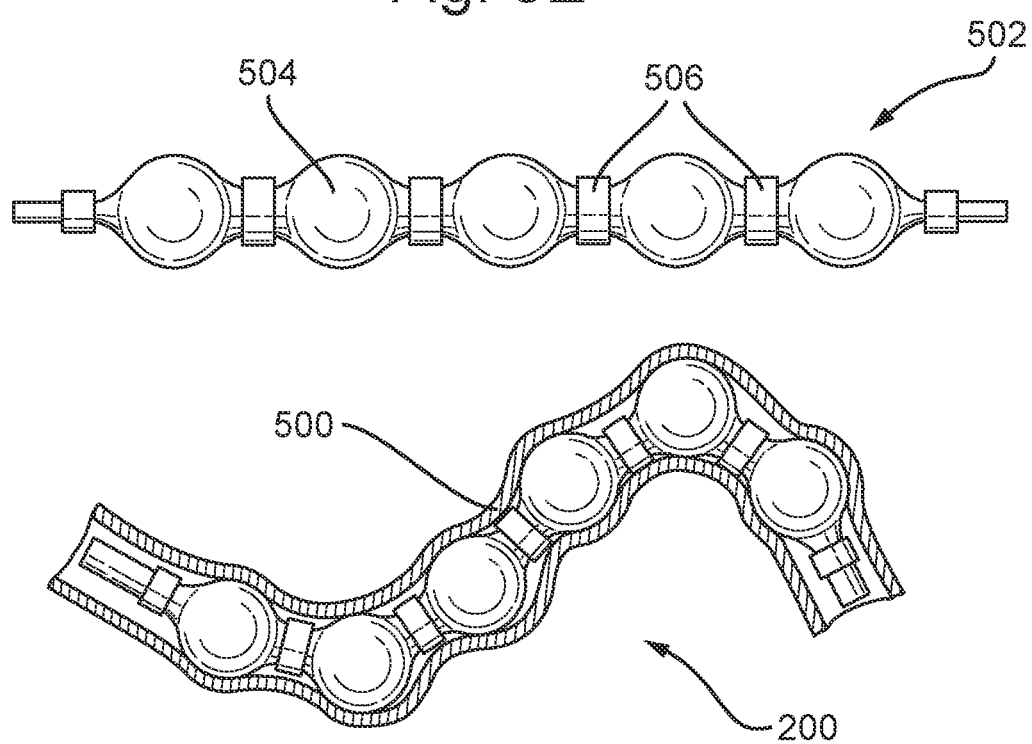

FIG. 3E shows a further embodiment in which a member 200 may be formed by a tube 500 and an expansion device 502 is located within the tube 500. The expansion device 502 may be formed from an inflatable (e.g., rubber) tube 504 around which are fixed a series of non-expandable rings 506 at regular intervals. The inflatable tube 504 may be pressurised (e.g., using air), and upon pressurisation the inflatable tube 504 may expand between the non-expandable rings 506. This causes the inflatable tube 504 to exert an increased pressure against the inner surface of the tube 500 and causes the member 200 to become substantially rigid, such that the member will be in its second, rigid state. Upon depressurisation of the inflatable tube 504 it will retract and exert less or no pressure against the inner surface of the tube 500, so that the member 200 will be in its first, flexible state.

Figure 3F:
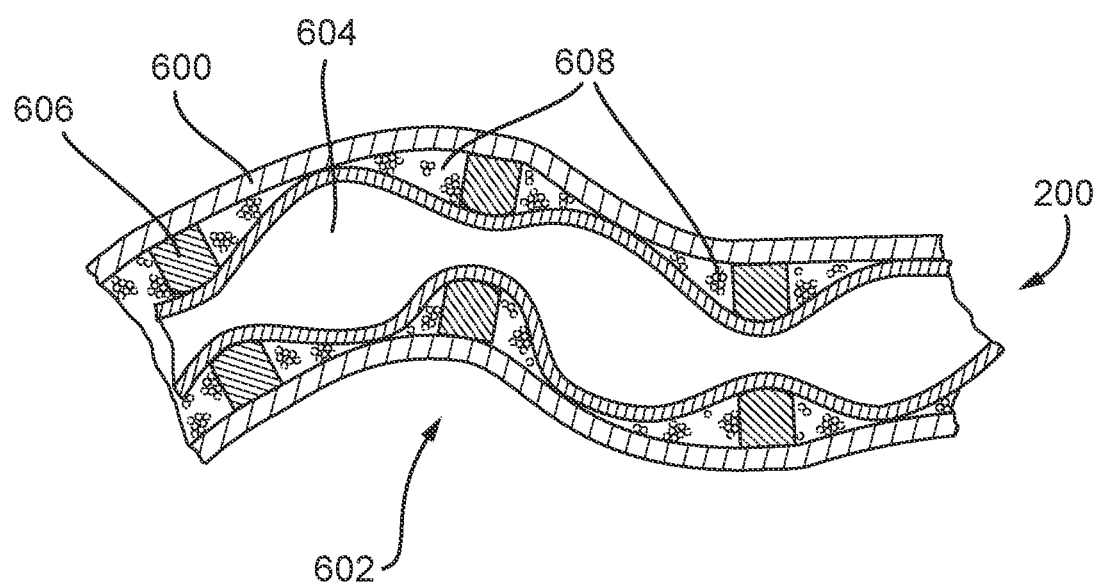

FIG. 3F shows a further embodiment similar to that of FIG. 3E, in which a member 200 is formed by a tube 600 and an expansion device 602 is located within the tube 600. The expansion device 602 may be formed from an inflatable (e.g., rubber) tube 604 around which are fixed a series of non-expandable rings 606 at regular intervals. The inflatable tube 604 may be pressurised (e.g., using air), and upon pressurisation the inflatable tube 604 may expand between the non-expandable rings 606. This causes the inflatable tube 604 to exert an increased pressure against the inner surface of the tube 600 and causes the member 200 to become substantially rigid, such that the member will be in its second, rigid state. Upon depressurisation of the inflatable tube 604 it will retract and exert less or no pressure against the inner surface of the tube 600, so that the member 200 will be in its first, flexible state.

In the FIG. 3F embodiment a powder, plurality of grains or spheres 608 are located within the spaces between the inflatable tube 604 and the inner surface of the tube 600. Upon expansion of the inflatable tube 604 the spheres 608 add to the pressure exerted against the inner surface of the tube 600 and assist in ensuring that the tube 600 is substantially rigid upon pressurisation of the inflatable tube 604.

Figure 3G:
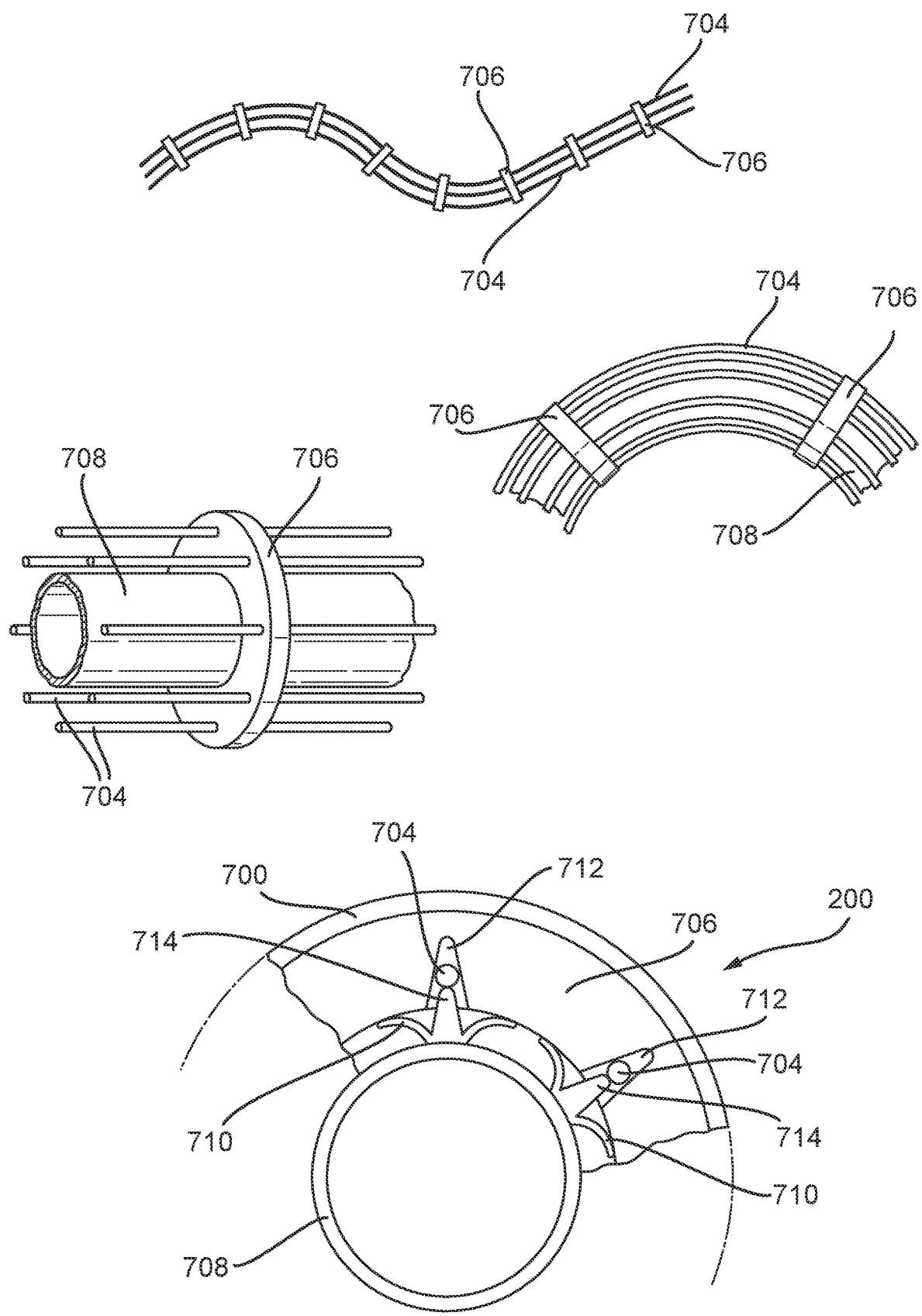

FIG. 3G shows a further embodiment in which a member 200 may be formed by a tube 700 and an expansion device 702 located within the tube 700. The expansion device 702 may comprise a plurality of wires 704 that run along the length of the tube 700. A plurality of lock members 706 may be attached to the tube 700, for example at regularly spaced intervals. The lock members 706 may be fixed in position with respect to the tube 700, such that the lock members 706 cannot move along the tube 700. The lock members 706 may, for example, be fixed to the inner surface of the tube 700 using adhesive. An inner expandable tube 708 may be located within the tube 700 and may be fixed to the lock members 706 via one or more resilient fixings 710.

Each of the plurality of wires 704 may pass through apertures or cavities 712 in the lock member 706. When the lock member 706 is in the form of a ring, the apertures 712 may extend around the circumference of the lock member 706. The resilient fixings 710 may each comprise a portion 714 (e.g., a pin) that extends at least partially into the aperture 712 so as to retain the respective wire 704 within the aperture 712.

When the member 200 is in its first, flexible state, the inner tube 708 may be depressurised and the wires 708 may pass freely through the apertures 712 upon movement or manipulation of the member 200. This allows the member 200 to be manipulated and moved into any desired position.

To switch the member 200 to its second, rigid state the inner tube 708 may be pressurised and this forces the resilient fixings 710 into the apertures 712, which traps the wires 704 therewithin and prevents their movement relative to the lock member 706. This means that the wires 706 are fixed in position, and prevents the manipulation or movement of the member 200.

Monitoring

Various embodiments of the present invention relate to the monitoring of a patient (or other user) when sitting or lying on a hospital bed. This is an important issue as conventional hospital beds have either inadequate monitoring systems, or are very complicated. The aim of these embodiments is to have a control system that can reduce the burden on hospital staff (or other care workers) and also improve generally the monitoring systems currently in use.

In accordance with an aspect of the present invention there is provided a method of monitoring a person on a bed. A control system may be provided to monitor the person, and communicate with one or more of the sensors described below in respect of the monitoring. The bed may be a bed as shown and described above in respect of FIG. 1, or FIGS. 2A-2B.

The method may comprise measuring and/or monitoring the weight of a person on the bed, for example using a weight sensor, e.g., a weighing scales operatively connected to the bed that is configured to measure the weight of the bed (including the person on the bed) as well as changes in the weight of the bed. Referring to FIG. 1, for example, a weighing scale may be connected to the bed support 12 or located on the base of the bed between the wheels 18. The weight of the person lying on the bed may be calculated by subtracting the weight of the bed without the person from the weight of the bed with the person.

The weight of the bed (and/or the person on the bed) could be monitored continuously. If this weight deviates by more than a predetermined amount, then a notification may be sent to the control system, which could then sound an alarm and/or record the time of the deviation, and the amount by which the weight deviated.

The method may comprise measuring and/or monitoring the temperature of the person on the bed, for example using one or more temperature sensors. The temperature sensors may be remote temperature sensors, such as one or more infrared temperature sensors. The temperature of the person on the bed may be monitored continuously.

The method may comprise measuring and/or monitoring the length or height of a person on the bed, for example using a suitable sensor or plurality of sensors. For example, one or more cameras may be placed above the bed, and may be configured to detect the top and bottom of the person's body on the bed. The control system may be configured to calculate the length of the person based on the response of the one or more cameras.

The method may comprise measuring and/or monitoring the pulse rate of the person on the bed, for example using a suitable pulse rate sensor. The sensor may be a remote and/or non-contact sensor (e.g., the sensor may be placed above the bed). The pulse rate of the person on the bed may be monitored continuously. If the pulse rate deviates by more than a predetermined amount, then a notification may be sent to the control system, which could then sound an alarm and/or record the time of the deviation, and the amount by which the pulse rate deviated. The control system may also relay the notifications and/or alarms, for example to a central server at a hospital for further processing, monitoring or recording.

The method may comprise measuring and/or monitoring the skin colour or tone of the person on the bed, for example using a suitable colour sensor. The colour sensor may be a remote and/or non-contact sensor. The skin colour or tone of the person on the bed may be monitored continuously. If the skin colour or tone changes significantly, or one or more predetermined colour hues are detected, then a notification may be sent to the control system, which could then sound an alarm and/or record the time of the deviation, and the amount by which the pulse rate deviated. The control system may also relay the notifications and/or alarms, for example to a central server at a hospital for further processing, monitoring or recording.

The motion of the person on the bed may be monitored, for example continuously and/or using one or more motion detectors.

One or more of the motion detectors may be configured to detect relatively large movements of the person on the bed (e.g., of the order of 10 cm or greater), and send a notification to the control system if the movement indicates that the person is having difficulty. For example, an algorithm may be used to predict if the person is about to fall off the bed (i.e., before it happens), and a notification could be sent and/or an alarm sounded if this is predicted. In some embodiments, for example those involving a bed having movable portions, some portions of the bed may move automatically in response to the prediction, to prevent the person falling off the bed.

Alternatively, or additionally, one or more of the motion detectors may be configured to detect relatively small movements (e.g., of the order of less than 10 cm) of the person on the bed, which typically indicate discomfort and uneasiness. These relatively small movements may be monitored over time, and one or more algorithms could be used to predict whether the person on the bed is in a serious amount of discomfort (e.g., due to bedsores), and a notification could be sent and/or an alarm sounded if this is predicted. In some embodiments, for example those involving a bed having movable portions, some portions of the bed may move automatically in response to the prediction, to prevent the person experiencing a serious amount of discomfort (e.g., a bedsore).

The control system may be configured to monitor one or more tubes that extend into the body of a person on the bed (i.e., an intubated person). One or more sound sensors may be provided to monitor the sound in the tubes, and the control system may be configured to detect specific sounds in the tubes, such as sounds that indicate discomfort or problems (e.g., mucus). The control system may be configured to detect specific sound waves (e.g., specific frequencies) and sound an alarm and/or send a notification if such waves are detected. The control system may also relay the notifications and/or alarms, for example to a central server at a hospital for further processing, monitoring or recording.

The method may comprise monitoring the respiration of a person on the bed. One or more remote sensors may be used, for example an impulse radar sensor, to detect and monitor breathing rates and patterns. This can be combined with the motion sensors described above to send both respiratory and motion data to the control system. The control system may then process this data to determine if the person on the bed is sleeping. The control system may continuously (or periodically) determine whether the person on the bed is asleep (using the respiratory and motion data) and output the status of the person (e.g., "awake" or "asleep") continuously (or periodically).

The control system may include an alarm configured to be activated based on a predetermined action by the person in the bed. The predetermined action may be selected by the person (or a nurse or care giver) based on their needs. For example, if the person cannot move their arms, then the predetermined action may be raising a leg by more than a given amount. Other predetermined actions include voice activation commands or other sounds, or eye movement. A user interface may include a menu with a number of predetermined actions to choose from, and the person on the bed (or a caregiver etc.) may be able to choose a suitable predetermined action from the menu, with which they can then use to sound an alarm.

All of the sensors described above, as well as optionally the control system may be mounted in a single housing, for example above the bed. The processing of the data may be carried out by the control system. This can help reduce the data processing and/or storage requirements of a server configured to process or store data relating to multiple beds. For example, hospitals may struggle to build and maintain servers that can process and store large amounts of data. By only sending certain notifications and/or alarms, the requirements for the central server may be reduced.

The control system may be configured to receive multiple data streams from a plurality of different sensors, for example any or all of the sensors described above, and combine these data streams for input into an analysis module or algorithm. The analysis module or algorithm may be configured to process the different data streams and output a combined health assessment. This may be based on data correlations and patterns that the algorithm may look for. As an example, the motion sensor may detect that the person on the bed has been moving uneasily in small amounts for ten minutes, and the temperature sensor may detect that their temperature is going down. This combination could signify a specific health problem that needs urgent attention. Upon detecting such a problem, the control system could relay a message for a caregiver (e.g., nurse or doctor) to visit the person urgently.

Although the present invention has been described with reference to preferred embodiments, it will be understood by those skilled in the art that various changes in form and detail may be made without departing from the scope of the invention as set forth in the accompanying claims.

The invention claimed is:

1. A support structure for a human or animal, the support structure comprising:
   a plurality of sections, wherein each section is movable relative to each other section and is configured to support a respective part of a body when the support structure is in use; and
   a plurality of resilient members, each resilient member extending in a longitudinal direction from an upper section of the support structure to a lower section of the support structure, wherein each resilient member is spaced apart from an adjacent resilient member in a transverse direction, and wherein each resilient member is elongated and has a wavy shape or profile conformable to a shape of the body;
   wherein a shape or profile of the support structure corresponds to a shape or profile of the plurality of resilient members.

2. The system of claim 1, wherein the control system is configured to output the alert or flag if the one or more characteristics (i) varies by more than a predetermined amount, (ii) remains outside a predetermined range of values for a predetermined time, or (iii) remains within a predetermined range of values for a predetermined time.

3. The system of claim 1, wherein the one or more characteristics includes a tension of the plurality of resilient members.

4. The system of claim 1, wherein the system is a bed and the support structure extends along the entire length of the bed and the plurality of resilient members provide primary support for a person or animal lying on the bed.

5. The system of claim 1, wherein the system comprises a bed comprising the support structure, wherein the support structure extends along the entire length of the bed and the plurality of resilient members provide primary support for the person or animal lying on the bed.

6. The bed of claim 1, wherein a first of the plurality of sections is configured to support an upper body portion, a second of the plurality of sections is configured to support an upper leg portion, and a third plurality of sections is configured to support a lower leg portion.

7. The support structure of claim 1, wherein the plurality of resilient members are biased between an upper holding member and a lower holding member, and are attached or connected to an at least one additional holding member between the upper and lower holding members, so as to form a predefined shape or profile, wherein the shape or profile of each of the plurality of resilient members changes upon relative movement of the plurality of sections due to the biasing between the upper and lower holding members and attachment or connection to the at least one additional holding member.

8. The support structure of claim 1 wherein the plurality of resilient members comprises at least 5 resilient members located in a parallel array across the support structure.

9. The support structure of claim 1, wherein the support structure is movable between a first configuration and second configuration, wherein the shape or profile of the support structure in the first configuration is different than the shape or profile of the support structure in the second configuration.

10. The support structure of claim 1, wherein the support structure is movable between a first configuration and a second configuration by relative movement of the plurality of sections, wherein the shape or profile of the support structure in the first configuration is different than the shape or profile of the support structure in the second configuration, wherein the shape or profile of the support structure is governed or controlled by movement of the plurality of sections and via the plurality of resilient members.

11. The support structure of claim 10, wherein the first configuration corresponds to a substantially flat or lying configuration, and the second configuration corresponds to an upright or seated configuration, wherein in the flat or lying configuration, the at least 5 resilient members exhibit at least one concave and/or convex portion.

12. The support structure of claim 10, wherein the processor is further configured to rotate one or more of the plurality of sections of the support structure so as to change a longitudinal profile of the plurality of resilient members such that the support structure moves between the first configuration and the second configuration, wherein the plurality of resilient members are biased so as to form a predefined shape and/or profile upon rotation of the plurality of sections of the support structure.

13. The support structure of claim 10, wherein the processor is further configured to rotate one or more of the plurality of sections of the support structure so as to change a longitudinal profile of the plurality of resilient members such that the support structure moves between the first configuration and the second configuration, wherein the plurality of resilient members are biased so as to form a predefined shape and/or profile upon rotation of the plurality of sections of the support structure.

14. The support structure of claim 1, wherein throughout any movement of the plurality of sections, the plurality of resilient members are configured to exhibit at least one concave and/or convex portion in the longitudinal direction.

* * * * *

UNITED STATES PATENT AND TRADEMARK OFFICE
CERTIFICATE OF CORRECTION

PATENT NO. : 11,554,061 B2
APPLICATION NO. : 16/347275
DATED : January 17, 2023
INVENTOR(S) : Jørn Refsnæs et al.

Page 1 of 1

It is certified that error appears in the above-identified patent and that said Letters Patent is hereby corrected as shown below:

In the Claims

At Column 23, Line 54 (Claim 1, Line 1):
"A support structure for a human or animal"
Should read:
--A system comprising:
a support structure for a human or animal--

At Column 23, Lines 59-60 (Claim 1, Lines 6-7):
"structure is in use; and
a plurality of resilient members"
Should read:
--structure is in use;
a plurality of resilient members--

At Column 23, Line 67 - Column 24, Line 3 (Claim 1, Lines 14-17):
"conformable to a shape of the body;
wherein a shape or profile of the support structure corresponds to a shape or profile of the plurality of resilient members."
Should read:
--conformable to a shape of the body; and
one or more sensors connected to one or more of the plurality of resilient members, and configured to determine one or more characteristics of the plurality of resilient members; and
a control system comprising a processor configured to monitor the one or more characteristics of the plurality of resilient members over time via the one or more sensors, and output an alert or flag based on an analysis of the one or more characteristics;
wherein a shape or profile of the support structure corresponds to a shape or profile of the plurality of resilient members.--

Signed and Sealed this
Thirteenth Day of June, 2023

Katherine Kelly Vidal
*Director of the United States Patent and Trademark Office*